US012109366B2

(12) United States Patent
Iselau et al.

(10) Patent No.: US 12,109,366 B2
(45) Date of Patent: Oct. 8, 2024

(54) URINARY CATHETER EXTENSION TUBE (71) Applicant: DENTSPLY IH AB, Mölndal (SE)

(72) Inventors: Frida Iselau, Landvetter (SE); Heikki Sojakka, Markaryd (SE)

(73) Assignee: DENTSPLY IH AB, Mölndal (SE)

( * ) Notice: Subject to any disclaimer, the term of this patent is extended or adjusted under 35 U.S.C. 154(b) by 0 days.

(21) Appl. No.: 17/236,837

(22) Filed: Apr. 21, 2021

(65) Prior Publication Data

US 2021/0330937 A1 Oct. 28, 2021

(30) Foreign Application Priority Data

Apr. 22, 2020 (EP) .................................... 20170827

(51) Int. Cl.
*A61M 25/00* (2006.01)
*A61L 29/04* (2006.01)

(52) U.S. Cl.
CPC ....... *A61M 25/0023* (2013.01); *A61L 29/043* (2013.01); *A61L 29/049* (2013.01); *A61M 25/0045* (2013.01)

(58) Field of Classification Search
CPC ........... A61M 25/0023; A61M 25/0045; A61L 29/043; A61F 2/844; B64G 99/00; E04B 1/34357; E04B 1/34378; E04B 1/32; E04C 2/40; E04C 2/427; E04H 15/32; Y10T 428/24686; A01G 9/00; A63H 33/16; B65D 81/03; B65D 59/04; B65D 71/36; B65D 59/08; B65D 71/14; B42D 15/00; F16L 55/11; F16L 57/00
See application file for complete search history.

(56) References Cited

U.S. PATENT DOCUMENTS

| | | | | |
|---|---|---|---|---|
| 4,681,573 A | * | 7/1987 | McGovern | A61F 5/4556 D24/112 |
| 4,755,421 A | * | 7/1988 | Manning | D04H 1/492 442/338 |
| 4,920,171 A | * | 4/1990 | Hutton, Jr. | D21H 21/20 428/913 |

(Continued)

FOREIGN PATENT DOCUMENTS

| | | | | |
|---|---|---|---|---|
| DE | 4343789 A1 | * | 5/1995 | A47K 11/06 |
| DE | 19916283 A1 | * | 10/2000 | A47K 11/12 |

(Continued)

OTHER PUBLICATIONS

Creased definition and meaning | Collins English Dictionary. https://www.collinsdictionary.com/dictionary/english/creased. Accessed Tue Sep. 19, 2023.*

(Continued)

*Primary Examiner* — Adam Marcetich
(74) *Attorney, Agent, or Firm* — Perkins Coie, LLP (57) ABSTRACT An extension tube for a urinary catheter comprises a tubular body with an inlet opening, an outlet opening and an internal lumen extending between the inlet opening and the opening. The tubular body comprising at least a first layer, which first layer includes natural and/or regenerated cellulose fibers, and preferably to a large extent, such as at least 40 wt %. The tubular body is further arranged to be compressible into a compacted, preferably generally flat, storage state, and to be expandable into an expanded, tubular use state.

22 Claims, 8 Drawing Sheets

(56) References Cited

U.S. PATENT DOCUMENTS

| | | | | |
|---|---|---|---|---|
| 4,937,890 | A * | 7/1990 | Tafur | A47K 11/12 604/350 |
| 5,401,263 | A * | 3/1995 | Cornellier | A61F 5/4556 4/144.2 |
| D374,281 | S * | 10/1996 | Markles | D7/700 |
| 5,566,400 | A * | 10/1996 | Jonec | A61F 5/453 4/144.2 |
| 5,722,136 | A * | 3/1998 | Jonec | A47K 11/06 604/326 |
| 6,460,200 | B1 * | 10/2002 | Mottale | A61F 5/4556 4/144.1 |
| 8,353,886 | B2 * | 1/2013 | Bester, Jr. | A61F 13/471 604/347 |
| 9,931,103 | B1 * | 4/2018 | DeLaRosa | A61F 5/4556 |
| 2003/0056283 | A1 * | 3/2003 | Wang | A61F 5/4556 4/144.4 |
| 2006/0090250 | A1 * | 5/2006 | Bolles | A47K 10/16 4/144.2 |
| 2006/0155216 | A1 * | 7/2006 | Flueckiger | A61F 5/4556 600/584 |
| 2007/0142794 | A1 * | 6/2007 | Bester, Jr. | A61F 5/453 604/354 |
| 2009/0299261 | A1 * | 12/2009 | Bognar | A61M 25/0045 604/99.01 |
| 2010/0193539 | A1 * | 8/2010 | Fathi | B65H 35/0026 221/45 |
| 2010/0263113 | A1 * | 10/2010 | Shelton | A61F 5/453 600/584 |
| 2015/0033460 | A1 * | 2/2015 | Mehta | E03D 11/025 4/301 |
| 2015/0273183 | A1 | 10/2015 | Foley et al. | |
| 2015/0306342 | A1 | 10/2015 | Rostami et al. | |
| 2016/0015225 | A1 * | 1/2016 | Pleyber | D21H 27/02 15/209.1 |
| 2018/0207323 | A1 * | 7/2018 | Chen | A61L 31/16 |
| 2018/0243532 | A1 * | 8/2018 | Willard | A61F 2/2427 |
| 2019/0321212 | A1 | 10/2019 | Palmer | |
| 2020/0023170 | A1 * | 1/2020 | Halstead | A61M 5/007 |
| 2020/0353207 | A1 * | 11/2020 | Vickers | A61M 39/12 |

FOREIGN PATENT DOCUMENTS

| | | | | |
|---|---|---|---|---|
| DE | 10103910 | A1 * | 12/2001 | A47K 11/12 |
| DE | 10046787 | A1 * | 4/2002 | A61F 5/453 |
| DE | 202014000528 | U1 * | 5/2014 | A61F 5/453 |
| EP | 1023882 | A1 | 8/2000 | |
| JP | 2006312001 | A * | 11/2006 | |
| JP | 3135627 | U * | 9/2007 | |
| JP | 3214813 | U * | 2/2018 | |
| JP | 7377579 | B1 * | 11/2023 | A47K 11/12 |
| KR | 101554710 | B1 * | 9/2015 | A61F 5/4556 |
| WO | WO-2006065909 | A1 * | 6/2006 | A61B 5/1076 |
| WO | 2019014344 | A1 | 1/2019 | |

OTHER PUBLICATIONS

GSC International 6302-10 Thermometer, Yellow Back, Total Immersion, Single Scale -20° C. to 110° C., 10 Pack. https://www.amazon.com/dp/B0BHLD29MG. Accessed Jul. 16, 2024. (Year: 2024).*

Extended European Search Report dated Nov. 6, 2020 for European Patent Application No. 20170827.8 (8 pages).

* cited by examiner

URINARY CATHETER EXTENSION TUBE

CROSS-REFERENCE TO RELATED APPLICATIONS

This patent document claims the benefits and priority of European Patent Convention Application No. 20170827.8, filed on Apr. 22, 2020, which is incorporated herein by reference in its entirety.

TECHNICAL FIELD OF THE INVENTION

The present invention relates to a urinary catheter extension tube, and to an extension tube assembly.

BACKGROUND

Urinary catheters are commonly used for draining urine from the bladder. Urinary catheters can be of an indwelling type, for long term use, such as days or even weeks, or for intermittent use, whereby the catheters are used for a single draining procedure, typically lasting a few minutes. Intermittent urinary catheters are e.g. used by a large group of persons for self-catheterization, which is a daily-life procedure, taking place several times a day. Typically, catheters for intermittent catheterization are used by patients suffering from urinary retention, due to e. g. spinal cord injury, Multiple Sclerosis or Prosthatic Hyperplasia. Using an intermittent catheter, the bladder may be drained through a natural or artificial urinary canal. Many catheters, such as those for intermittent catheterization, are provided with a hydrophilic coating or the like, providing a smooth and slippery surface when wetted, for safe and comfortable insertion in the urinary canal.

Indwelling catheters are normally connected to a urine collection bag, whereas intermittent urinary catheters are often used to drain urine directly into a toilet or the like. To facilitate such use, in particular for situations where the users have difficulty in coming sufficiently close to the toilet, and to avoid the need to move over to the toilet seat, it is known to use extension tube, which conveys the drained urine from the discharge outlet of the catheter and into the toilet. It is also known to use the catheter package as an extension tube.

However, such known urinary catheter extension tubes are often difficult to handle for the user, e.g. in maintaining the extension tube properly in place to receive the urine drained from the catheter discharge outlet, in maintaining the extension tube outlet properly located to drain the urine into the toilet or the like, to avoid kinking and other obstruction of the flow path through the extension tube during the draining, and the like.

Further, known extension tubes are often relatively expensive, and are for this reason often reused several times. However, taking care of the used extension tube, by cleaning it and storing it in an adequate manner after use, is cumbersome and tedious. Also, when the extension tubes are not reused, the user would often not want to dispose a used extension tube in waste disposal units in public restrooms and the like, in order to maintain discretion. For this reason, there is also a need to take care of the extension tube after use, by arranging it in a package, and possibly clean it first to avoid odor and accidental spilling of remaining urine.

Further, often users of intermittent urinary catheters have limited or diminished dexterity, e.g. as a result of spinal cord injuries, which makes the above-discussed handling even more complicated and cumbersome.

Further, known extension tubes are relatively bulky, making the extension tubes difficult to carry round in a discrete manner.

Thus, there is a need for a urinary catheter extension tube which can be handled more easily, and in particular for users having poor dexterity. There is also a need for a urinary catheter assembly which can be produced more cost-efficiently. Further, there is a need for a catheter extension tube which is smaller, and easier and more discrete to carry around by the user in his/her daily life, and easier and more discrete to dispose of after use.

SUMMARY OF THE INVENTION

It is therefore an object of the present invention to provide a urinary catheter extension tube which at least alleviates the above-discussed problems.

This object is obtained by means of a urinary catheter extension tube in accordance with the appended claims.

According to a first aspect of the invention there is provided an extension tube for a urinary catheter, comprising a tubular body with an inlet opening, an outlet opening and an internal lumen extending between said inlet opening and outlet opening, said tubular body comprising at least a first layer, said first layer including natural and/or regenerated cellulose fibers, and wherein the tubular body is arranged to be compressible into a compacted, preferably generally flat, storage state, and to be expandable/erectable into an expanded/erected, tubular state.

When in the compacted storage state, the extension tube is very small, and may e.g. be arranged as a roll. In this compact storage position, the extension tube could easily be carried around discretely, e.g. in a handbag, in a pocket or the like, without attracting notice.

When in the compacted storage state, the extension tube is preferably compacted to a relatively, or entirely, flat state. However, other way of compacting the tube are also feasible, as would be appreciated by the skilled reader.

When the extension tube is to be used, it is expanded/erected into the expanded/erected use state, and can thereby function as an extension tube, providing a prolongation of the fluid path of the urinary catheter. Hereby, the drained urine can be discharged into e.g. a toilet even when the user is at some distance from the toilet.

After use, the extension tube may be directly discarded. However, it may prior to that be at least to some extent compacted again, thereby making it less noticeable if discarded. Alternatively, the again compacted extension tube may also be arranged in a storage package, and then be carried by the user in the same discrete way as before use, to be discarded later.

The material preferably comprises at least 40 wt % of natural and/or regenerated cellulose fibers. Since the material of the extension tube is preferably to a large, or very large, extent made of cellulose, the material may, in one embodiment, be arranged to disintegrate after a relatively short time when immersed in water. This makes it possible also to discard the extension tube also in the toilet, to flush it down. In doing so, the extension tube will after a while disintegrate similar to ordinary toilet paper. This may be referred to as a flushable extension tube.

Regardless of whether the extension tube is flushable or not, the material of the extension tube is preferably chosen and arranged so that the extension tube remains relatively intact and stable when water or urine flows through its internal lumen during a determined use time period, i.e. at least for a period of time sufficient to drain urine from the bladder, such as for at least 5 minutes, and preferably at least 10 or 15 minutes. Preferably, the material is also arranged to resist, at least to a large extent, transfer of moisture from the interior surface of the extension tube to the exterior surface during this determined use time period.

In the context of the present application, whether the extension tube remains relatively intact and stable when water or urine flows through its internal lumen during a determined use time period may e.g. be determined by a simple test procedure, such as by placing the tube on two supports, such as two bars, in the vicinity of the inlet and outlet openings of the extension tube, and with no support therebetween, and in a relatively horizontal position, but with some minor inclination to provide a flow through the tube. Water or urine is then continuously poured into the inlet opening. If the extension tube remains intact, i.e. resist collapsing, during the determined time, and without any significant leakage, the extension tube has passed the test.

A relatively high resistance to urine, and a relatively low absorption, is also of advantage if the extension tube is e.g. discarded in a waste basket or the like, to reduce the odor.

At the same time, in case a flushable extension tube is wanted, the material of the extension tube is preferably hydrodegradable, and chosen and arranged so that the extension tube to a large extent disintegrates when immersed in water, such as within a period of time sufficient to make the extension tube flushable. For example, the extension tube could be arranged to be sufficiently disintegrated when immersed in water for a few hours or less. By hydrodegradable is here meant a material which breaks down or disintegrates, preferably by hydrolysis, when placed in an aqueous environment, such as when being immersed in water.

The first layer preferably includes at least 50 wt % of natural and/or regenerated cellulose fibers, such as at least 60 wt %, at least 70 wt %, at least 80 wt %, at least 90 wt %, or at least 95 wt %.

In one embodiment, the first layer is made primarily of natural cellulose fibers, such as paper.

Additionally, or alternatively, the layer may comprise regenerated cellulose fibers, such as viscose, and preferably viscose without any filler material.

The tubular body may be formed by the first layer as a single layer. Hereby, the tubular body may be formed essentially entirely by the first layer.

Alternatively, the tubular body may comprise at least one additional layer, said additional layer forming a laminated construction with said first layer. The additional layer(s) may also be cellulose based layers, such as paper, but may have different properties than the first layer, such as being more or less water resistant, more or less rigid, etc. However, an additional layer may also be made of a non-cellulose based material, such as a thin coating of thermoplastic polymer.

In case additional layers are provided, the first layer is preferably the thickest layer.

In case one or more additional layer(s) is used, the first layer may be arranged as an innermost layer, facing the internal lumen of the tube, or as an outermost layer, forming the exterior surface of the tube. In case more than one additional layer is used, the first layer may also be an intermediate layer, arranged between the two or more additional layers.

In addition to the cellulose fibers, the cellulose based material, and in particular the first material, may comprise additives, such as one or more of fillers, pigments, wet strength chemicals, retention chemicals, cross-linkers, softeners or plasticizers, adhesion primers, wetting agents, biocides, optical dyes, hydrophobizing chemicals such as alkyl ketene dimer (AKD), alkyl succinic anhydride (ASA), waxes, resins etc.

The fillers may be any fillers known to be used in papermaking, such as mineral fillers like kaolin, china clay, titanium dioxide, gypsum, talc, chalk, ground marble, ground calcium carbonate and precipitated calcium carbonate.

Preferably, one or more sizing additives, such as e.g. rosin, liquid paraffin wax, alkyl ketene dimer (AKD), alkyl succinic anhydride (ASA), etc., may be added to the cellulose material to provide a desired water absorbency profile for the material.

In embodiments where AKD is used, the content of AKD is preferably in the range of 0.1-10 wt %, and preferably in the range 0.5-5%, and most preferably in the range 1-2 wt %.

In embodiments where polylactic acid (PLA) is used, the content of PLA is preferably in the range of 0-50 wt %, and preferably in the range of 1-45 wt %, and more preferably in the range of 5-40 wt %, and even more preferably in the range of 10-35 wt %, and most preferably in the range of 20-30 wt %. Inclusion of PLA in the material makes the material more rigid.

The wet strength additives may e.g. be polymers, such as polyacrylamide (PAM), or starch.

In a preferred embodiment, there is a high content of cellulose, and only additives to increase the hydrophobicity and optional fillers are added.

The cellulose based material can be produced in a papermaking machine, such as a any conventional type of machine known to the skilled person used for the production of paper, paperboard, or similar products. The material is formed as a wet web, which is then dried. In order to increase the shape stability and memory of the material, the dewatering may occur in an at least partly shaped and erect form, such as by being placed on suitably arranged wires. The dewatering may also include subjecting the web to heat, vacuum, ultrasound or the like. After dewatering and drying, the material may also be dried or smoothened by soft or hard nip, calendars etc.

The cellulose fibers of the material may be wood cellulose fibers, both from hardwood or softwood fibers. However, the cellulose may also be from other sources, such as agricultural fibers such as wheat straw pulp, bamboo, bagasse, or other non-wood fiber sources. The material is preferably made from pulp including pulp from virgin fiber, e.g. mechanical, chemical and/or thermomechanical pulps. It can also be made from broke or recycled paper, i.e. recycled fibers.

The material may also include nanocellulose, such as a cellulose nanofiber material containing multiple elementary fibrils with both crystalline and amorphous regions. In this case, the nanocellulose may be included together with other cellulose in a layer, or arranged in a separate layer. By using nanocellulose the material becomes more stable and rigid in shape, with an increased shape memory, and is also more water resistant than other cellulose materials. The nanocellulose may be wood- or plant-based, and may be chosen from cellulose nanofibrils (CNF) or cellulose nanocrystals (CNC), preferably cellulose nanofibrils. This ensures that the raw materials for the cellulose product are obtained from an abundant, renewable and biodegradable source.

The material forming the extension tube, regardless of whether it is a single layer material or a laminated material having two or more layers, preferably has a surface weight in the range of 50-180 g/m$^2$, and preferably 70-170 g/m$^2$, and most preferably 90-130 g/m$^2$. If the cellulose has thicker and longer fibers, a thinner material, may be provided, having essentially the same properties.

The absorbance of the material is a measure of how much and fast water is absorbed by the material. This may be measured as a Cobb value, and e.g. in accordance with the ISO 535:014 standard. In a test for measuring Cobb values, a water pillar is arranged over the material to be measured for a predetermined time. The water should be of room temperature, typically 23 degrees C. The weight of the material is measured before and after wetting, after having removed the water pillar and any remaining residual water, e.g. by a swift wiping with a wipe. The difference in weight constitutes the weight of the absorbed water. Different wetting times may be used, such as 60 seconds, 120 seconds, but longer and shorter periods may also be used. However, according to the standard procedure, the actual time during which the material is exposed to the water pillar is less than the indicated wetting time, to provide time to wipe of remaining water on the surface and the like. Thus, for a wetting time of 60 seconds, the exposure to the water pillar is 45 seconds, but the weighing is made after 60 seconds. In the present application, the Cobb values refer to measurements where the wetting has been made for 60 seconds—i.e. Cobb-60 values.

A low Cobb value means that only a small amount of water is absorbed, which is of advantage since it means that the material maintains its shape and rigidity even after some period of wetting, and that there is less odor from the material if stored (when wetted by urine). A higher Cobb value means that a greater amount of water is absorbed. This generally means that the material will dissolve/disintegrate more easily during wetting. Thus, finding a material with an adequate Cobb value is an indication that the material may both remain stable and rigid enough during drainage through the tube, and also be easily dissolved/disintegrated after use, e.g. when being flushed into the toilet.

In embodiments where a single cellulose based layer is used, i.e. only the first layer, it preferably has a low absorbance, measured as a Cobb value, in the range of 5-50 g/m². Preferably, the Cobb value is in the range of 10-30 g/m², and most preferably in the range 10-20 g/m².

In embodiments where two or more cellulose based layers are used, the inner layer may have a lower Cobb value, and the outer layer may have a higher Cobb value. In such embodiments, the inner layer may have a Cobb value in the range of 5-50 g/m², and preferably in the range 10-30 g/m², and most preferably in the range of 10-20 g/m². The outer layer may have a Cobb value of at least 50 g/m², and preferably at least 70 g/m², and more preferably at least 80 g/m², and most preferably at least 100 g/m². The Cobb value of the outer layer may be in the range of 50-150 g/m², and preferably in the range 70-130 g/m², and most preferably in the range of 80-110 g/m². The Cobb value of the outer layer may also be above 150 g/m², such 200 g/m² or more.

In one embodiment, the Cobb value on the inside surface is preferably less than 30 g/m², and the Cobb value on the outside surface is preferably more than 100 g/m².

The material of the tubular body is preferably arranged to be more water resistant, and have greater water repellency, on the internal surface, i.e. facing the internal lumen, than in the middle of the wall, and/or on the external surface.

To this end, a chemical surface sizing agent, surface treatment agent or the like may be added to the internal surface, and optionally also to the external surface. For example, the surface can be made more dense and compact using a biobased composition, such as starch. The surface can also be made more hydrophobic by suitable additives.

Additionally, or alternatively, when a laminated material is used, the inner layer may be a cellulose based layer having less absorbency, and greater water resistance, than another layer, such as an outer layer and/or an intermediate layer.

In another embodiment, when a laminated material is used, a thin layer of a hydrophobic organic material or the like, such as polyactic acid (PLA), may be arranged on the interior surface, as a coating. It is also possible to use a silicone-based layer, starch-based layer, clay-based layer, polyethylene (PE) layer, or other thermoplastic polymer layers, and the like. Instead of being laminated, such a layer may also be provided in the form of spray or dip coating, or the like. A layer including nano-cellulose may also be used towards the interior surface.

Since the extension tube is made primarily of cellulosic material, the extension tube is biodegradable and non-toxic, making it very environmentally friendly. By a biodegradable material is here meant an organic material which breaks down by microorganisms, such as bacteria and fungi, in a microbial process, and preferably under environmental exposure, e.g. making the material compostable. A biodegradable material may also be biodegradable in accordance with any of the standards ASTM D6868 and EN 13432, and may also be compostable in accordance with the standard ASTM D6400.

The tubular body preferably has a plurality of longitudinally extending fold lines, extending along the axial direction of the tubular body. At least two of the longitudinally extending fold lines are preferably arranged oppositely to each other, separated by the same circumferential distance along the tubular body in both directions. Such fold lines make the extension tube easier to compact into the compact, essentially flat, storage state, and also enhances the rigidity of the extension tube when erected into the erected use state.

The tubular body, when in an erected use state, may have a polygonal cross-section. In one embodiment, the tubular body, when in the erected state, has a quadrilateral cross-section, and preferably a cross-section formed as a parallelogram, and most preferably a cross-section formed as a rhombus or a rectangle. The polygonal cross-section is preferably provided by arranging fold lines in the corners or edges of the polygon. In a parallelogram cross-sectional configuration, each side may e.g. have a length in the range of 0.5-1 cm.

In order to facilitate the folding, and also to make the extension tube more stable in the erected use state, so that it remains in the erected use state once erected, the folding lines may be provided in the form of creased folding lines. The creased folding lines are provided with an indentation or protrusion at the center of the folding line, forming a convex or concave bead in the folding line. Such creasing facilitates the folding, and may provide a memory in the material, to make it automatically resume the erected use state when unobstructed, and to remain in this state during use. Such creasing may be used for all the fold lines, but may alternatively only be used for some of the fold lines, such as for two adjacent fold lines, or for two opposed fold lines.

An adequate memory in the material, to make it at least to some extent strive to resume the erected use state, may also be provided in other ways. For example, the extension tube may be dried in an at least partly erected state during production, before being compacted.

The extension tube may be formed by a single sheet of material, either comprising a single layer or two or more layers. To form a tube, two sides of the sheet may be connected to each other, preferably with an overlap to provide a strong connection. The connection may be formed by an adhesive, such as a hot melt adhesive. The adhesive is preferably biocompatible.

The overlap may be arranged to extend over one of the edges formed by the fold lines, such as extending over two sides of a polygonal cross-section. Hereby, the material will be doubled over at least some part of the extension tube, thereby adding to the structural stability and the water resistance. Such doubled layers may e.g. be arranged on parts intended to be lowermost in use.

In one embodiment, the overlap extends over essentially the whole of at least one side extending between two folding lines. In another embodiment, the overlap extends over at least two folding lines. In another embodiment, the overlap extends over a folding line, and over essentially the whole of at least two sides extending between folding lines.

The tubular body may have a length in the range of 30-70 cm, and preferably in the range of 35-65 cm, and more preferably in the range of 40-60 cm. However, the extension tube may also be provided in much longer lengths, allowing the user to cut the extension tube in to any desired length for every use occasion.

The extension tube may also be provided with markings indicating a length along the longitudinal, axial direction of the extension tube. Such markings may e.g. be in the form of a scale, with numbers indicating various lengths in e.g. cm or inches, similar to the scale on a ruler. However, the markings may also be in other forms, such as symbols arranged at a certain distance from each other, such as every 5 cm, or colored or otherwise marked areas sequentially extending over a certain length, such as 5 cm. Such markings facilitate cutting or severing of the extension tube into any desired, shorter length. Hereby, the length of the extension tube can easily be customized for the user's needs. For example, a user may have preferences to always use an extension tube of a specific length, whereas other users may want to choose the length of the extension tube in dependence of the specific situation for every urine drainage procedure, such as the height of the toilet, the accessibility of the toilet from a wheelchair, or the like.

In particular, such markings are of great use when the extension tube is provided in large lengths, e.g. on a roll, and e.g. with the use of a dispenser, as will be discussed in the following.

The body, in the expanded/erected use state, preferably has a maximum cross-sectional extension in the range of 0.5-3 cm, and preferably in the range of 1-2.5 cm. Such cross-sectional dimensions are useful both for allowing unrestricted flow of urine through the extension tube during the urine drainage procedure, and also to allow a discharge end of the catheter to be inserted into the inlet opening of the extension tube during use. A urinary catheter often has a flared, somewhat enlarged rearward end, often referred to as funnel or connector, and the extension tube is preferably dimensioned to allow insertion of such an enlarged catheter end.

However, alternatively, the extension tube may be dimensioned, at least at one end thereof, to be inserted into a flared, enlarged rearward end of the catheter.

The urinary catheter, to be used with the extension tube, normally comprises one or several drainage openings, so-called eyes or eyelets, arranged at or in the vicinity of the proximal insertion end, and internal lumen inside the catheter shaft, leading from the eyes to a discharge end. A part of, or the whole, catheter shaft may further be provided with a hydrophilic coating, or in other ways been provided with a hydrophilic surface, which exhibits a lowered friction when wetted. Further, the distal part may, at least on a part thereof, have larger cross-sectional dimensions than the catheter shaft. The distal part may e.g. be flared or funnel shaped, increasing in dimension towards the distal end, thereby making it easier to maintain the extension tube in a correct position during use.

The catheter is preferably a urinary catheter for intermittent, short time use. The term "short term use" indicates a use that is limited in time, and in particular limited to a time period of less than 15 minutes, and preferably less than 10 minutes, and most preferably less than 5 minutes.

In use, the drainage end of the catheter is inserted into the inlet opening of the extension tube and is maintained in this position during the whole drainage procedure.

The extension tube may be arranged to remain in place over the end of the catheter by means of friction between the internal sides of the extension tube and the external walls of the catheter discharge end. To increase this friction, the extension tube may also be provided with friction enhancing elements, such as an internal coating with increased friction close to the inlet end, corrugations, a flange, or other type of indenting or protruding parts to interact with the catheter discharge end, or the like. In one embodiment, the end of the extension tube may be provided with a crinkly texture with a creasing process, such as creping.

Additionally, or alternatively, the user may manually hold the extension tube in place over the catheter discharge end during use, e.g. by pressing the extension tube towards the catheter discharge end with a two finger grip or the like.

Additionally, or alternatively, an external connection element may also be used, such as a rubber band, an adhesive tape, a strap, or the like, in case a tighter seal is desired.

According to another aspect of the invention, there is provided an extension tube assembly comprising:
  an extension tube as discussed above, wherein the extension tube is arranged in a compacted state in a roll; and
  an extension tube dispenser for housing said roll, the roll being rotatably arranged, and comprising a cutter for severing a length of dispensed extension tube from said roll.

With the dispenser, the user may at every time dispense and sever the desired length of the extension tube. This is even more facilitated when markings are provided on the extension tube.

The roll may comprise an extension tube sufficient for multiple uses. For example, the roll may comprise an extension tube of a length of a meter or more, such as 2 m or more, 5 m or more, or even longer.

The dispenser is preferably arranged to enable replacement of the roll of the extension tube. Hereby, the dispenser may be reused over time.

The cutter may be arranged as a fixed serration, as in a conventional adhesive tape dispenser, whereby the extension tube may be pulled downwards towards the serration to make the cut.

In an alternative embodiment, the cutter may comprise a hinged, jaw-like serration element, whereby the cutting is made by clamping the cutter over the extension tube to sever it.

The dispenser may comprise a housing including: opposite sides; a hub extending from at least one side, the hub being adapted to hold a roll of extension tube for rotation within the housing; a bridge connecting the sides; and a cutter pivotably connected to the bridge, the cutter being adapted to cut the extension tube. The cutter may comprise a plurality of cutting teeth. The hub may comprise a single hub, or two hub portions, one extending from each side of the housing, the hub portions interlocking to form the hub.

The dispenser it preferably minimally larger than the roll of extension tube held by the dispenser. In an embodiment, the dispenser is of a palm size, thereby making it easy to use and easy to carry around. Preferably, the dispenser is minimally larger than the roll of extension tube held by the dispenser.

These and other aspects of the invention will be apparent from and elucidated with reference to the embodiments described hereinafter.

BRIEF DESCRIPTION OF THE DRAWINGS

For exemplifying purposes, the invention will be described in closer detail in the following with reference to embodiments thereof illustrated in the attached drawings, wherein:

FIGS. 2a-c illustrate an extension tube in accordance with an embodiment of the invention, wherein

FIG. 10 is a schematic side-view illustrating use of the extension tube of FIG. 2a;

FIGS. 13a-b are illustrations of a dispenser useable for dispensing an extension tube from a roll, in accordance with an embodiment of the present invention, where

DETAILED DESCRIPTION OF PREFERRED EMBODIMENTS

In the following detailed description preferred embodiments of the invention embodiments are exchangeable between the embodiments and may be combined in different ways, unless anything else is specifically indicated. It may also be noted that, for the sake of clarity, the dimensions of certain components illustrated in the drawings may differ from the corresponding dimensions in real-life implementations of the invention, e.g. the length, width and height of the extension tube, etc.

The extension tube is arranged to cooperate with a urinary catheter, so that a discharge end of the urinary catheter is inserted into an inlet end of the extension tube, and held in place in this position during the drainage of urine.

Figure 1:
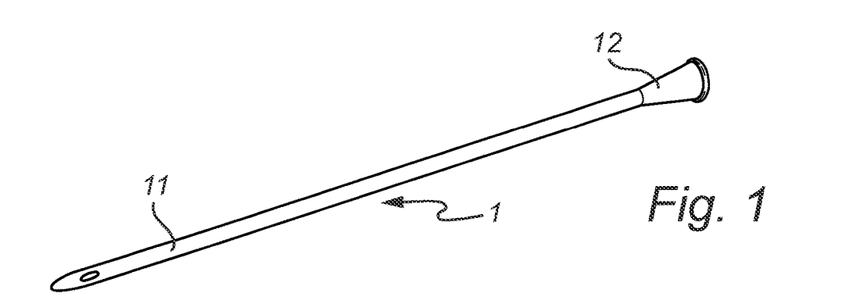
FIG. 1 is an illustration of an exemplary urinary catheter, for use with an extension tube in accordance with an embodiment of the present invention.

An exemplary urinary catheter, illustrated schematically in FIG. 1, comprises a catheter 1 having an insertable section 11, comprising an insertable, proximal part, with an insertion tip, and a catheter shaft, and a non-insertable section 12, a distal part, forming a funnel or connector part and the discharge end. The non-insertable section 12 preferably has a larger diameter than the insertable section 11 at least on a part thereof. The rear end of the non-insertable section may be flared or funnel-shaped, and may be arranged to be connected to a tapered connection part of a urine collection bag or the like. However, the non-insertable section may alternatively have a relatively uniform cross-sectional area.

Extension Tube

Figures 2A, 2B:
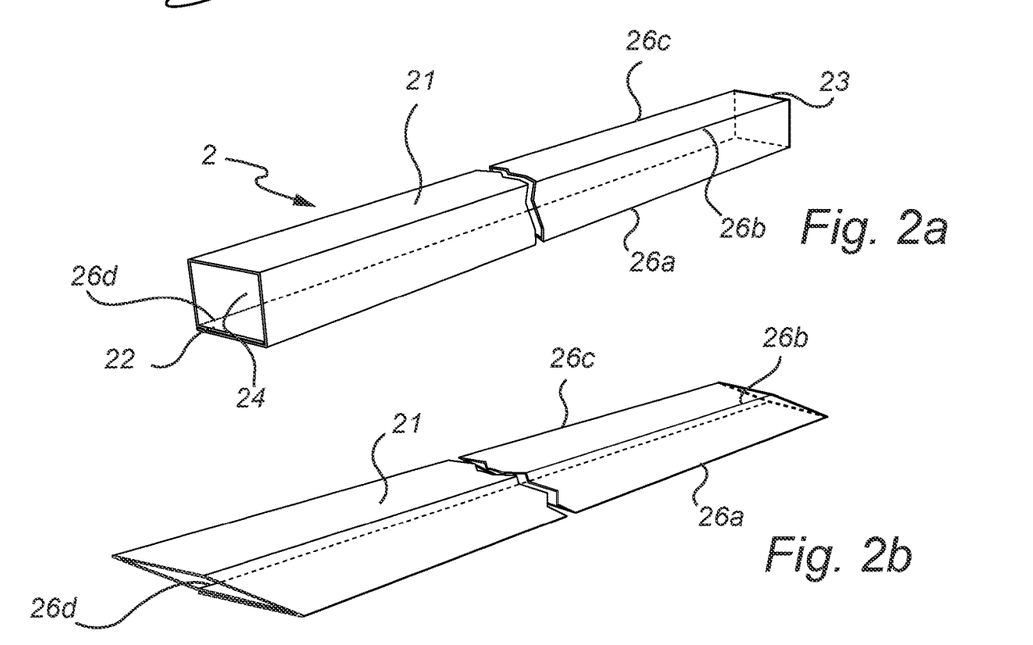
FIG. 2a is a perspective view, illustrating the extension tube of one embodiment in an erected use state.
FIG. 2b is a perspective view illustrating the extension tube of FIG. 2a in a compacted storage state.
Figure 2C:
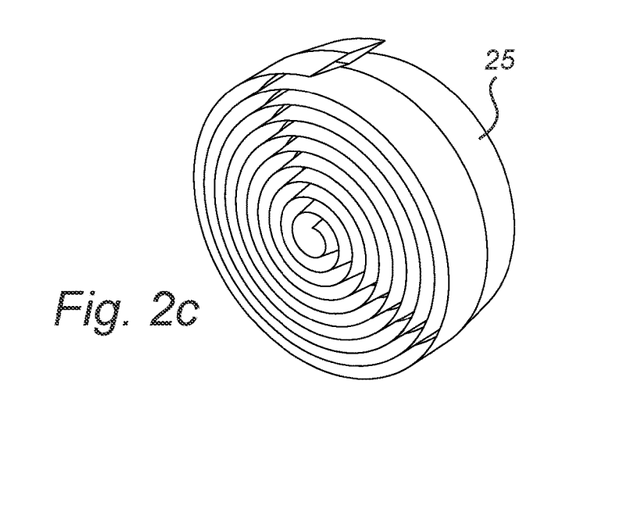
FIG. 2c is a side-view illustrating the extension tube of FIG. 2a in a compacted storage state, and arranged as a roll.

Referring to FIGS. 2a-c, an embodiment of the extension tube 2 comprises a tubular body 21 with an inlet opening 22, an outlet opening 23 and an internal lumen 24 extending between the inlet opening 22 and the outlet opening 23. The tubular body is arranged to be compressible into a compacted, generally flat state, as illustrated in FIG. 2b, and to be erectable into an erected, tubular state, as illustrated in FIG. 2a.

When in the compacted storage state, the extension tube is very small, and may e.g. be arranged as a roll 25, as illustrated in FIG. 2c. In this compact storage position, the extension tube could easily be carried around discretely, e.g. in a handbag, in a pocket or the like, without attracting notice. To maintain the roll in the rolled-up condition, a tape may be provided on the end of the extension tube, a strap or rubberband may be arranged around the roll, or the like. The roll may also be provided in a package, such as a bag, maintaining the rolled-up shape.

The tubular body preferably has a plurality of longitudinally extending fold lines 26a-d, extending along the axial direction of the tubular body. At least two of the longitudinally extending fold lines are preferably arranged oppositely to each other, separated by the same circumferential distance along the tubular body in both directions. In the illustrative example of FIGS. 2a-c, four fold lines 26a-d are provided, with the fold lines 26a and 26c and the fold lines 26b and 26d, respectively, being arranged oppositely to each other, separated by the same circumferential distance along the tubular body in both directions. Thus, the extension tube here has a cross-section shaped as a parallelogram, and with the cross-section in the erected use state being shaped e.g. as a rectangle, with two opposite sides being of one length and two other opposite sides being of another length, or a square, with all the sides being of the same length.

Referring to FIGS. 2d-2h, the extension tube may also be provided with a flange, which may protrude out from the tube wall. The flange can be used as a handle, for gripping and holding the tube during use. In addition, the flange adds structural stability to the tube, thereby further resisting collapse of the tube during use.

Figures 2D, 2E, 2F:
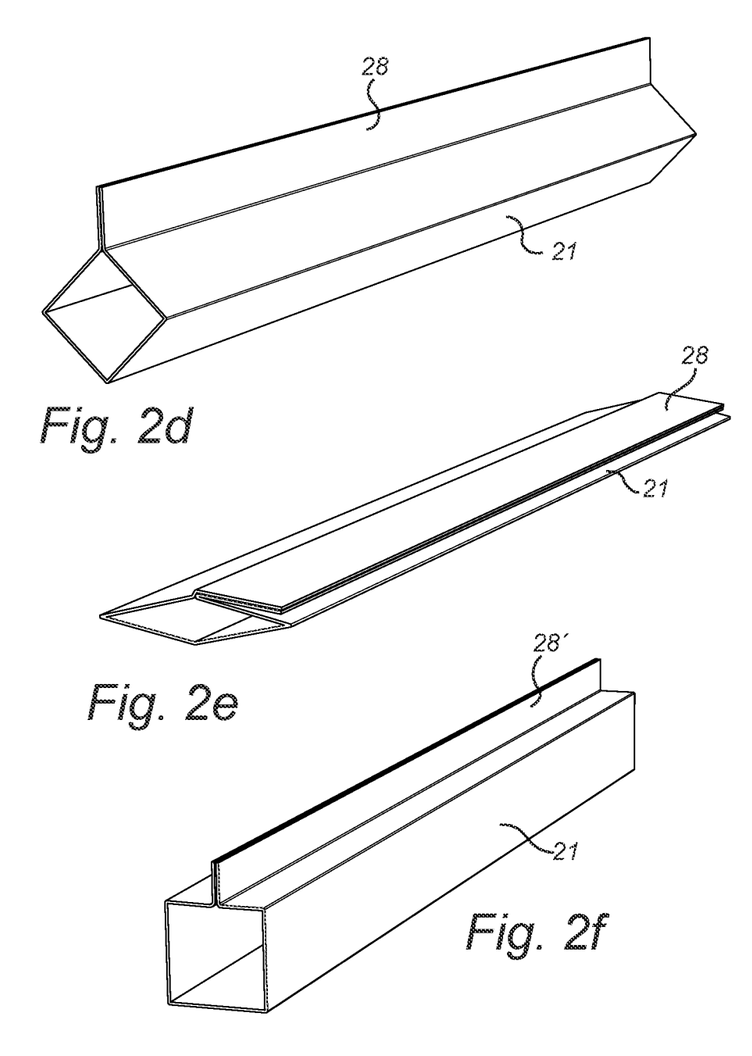
FIG. 2d is a perspective view illustrating the extension tube of another embodiment in an erected use state.
FIG. 2e is a perspective view illustrating the extension tube of FIG. 2d in a compacted storage state.
FIG. 2f is a perspective view illustrating the extension tube of yet another embodiment in an erected use state.

In the embodiment illustrated in FIGS. 2d and 2e, the extension tube 21 comprises a flange 28, forming an elongate tab, which is arranged in one of the folded edges of the tube, i.e. along and connected to one of the fold lines. The flange has here been formed by making adhering two ends of a sheet together at the flange. Thus, in this embodiment, the flange and the walls of the tube is made of the same sheet of material, and the side wall comprises a single ply of the sheet, whereas the flange comprises two plies, joined together. Thus, the flange in this embodiment has a thickness which is essentially doubled compared to the wall thickness of the tube.

In the erected use position, the flange is preferably arranged to protrude out from the tube, as illustrated in FIG. 2d. In the compacted storage position, the flange may be folded down over the side of the tube, as illustrated in FIG. 2e.

Figure 2G:
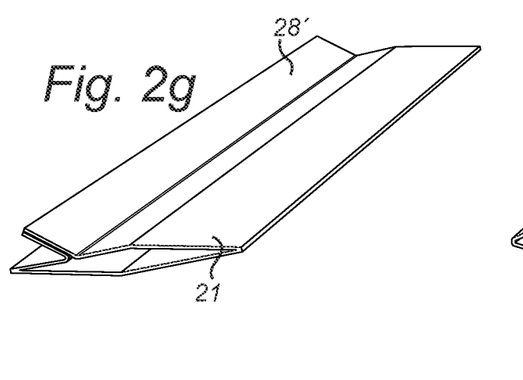
FIG. 2g is a perspective view illustrating the extension tube of FIG. 2f in a compacted storage state.

The embodiment illustrated in FIGS. 2f and 2g, is similar to the embodiment discussed with relation to FIGS. 2d and 2e, and the flange 28' is formed and used in the same way. However, in the embodiment of FIGS. 2f and 2g, the flange is arranged in the middle of one of the sides of the tube, and at a distance from all the edges/folding lines.

Figure 2H:
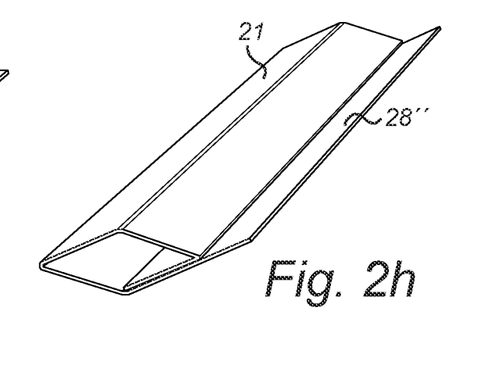
FIG. 2h is a perspective view illustrating the extension tube of yet another embodiment in an erected use state.

In yet another embodiment, illustrated in FIG. 2h, the flange 28" is arranged connected to one of the edges/folding lines, in the same way as in the embodiment discussed in relation to FIGS. 2d and 2e. However, in this embodiment, the tube is formed by connecting one free end of the sheet forming the tube to one of the side walls, thereby providing wall with two plies and a double thickness. The other free end extends out from the tube, thereby providing the flange 28". In this embodiment, the flange is made of a single ply. The tube is formed with at least one side wall made of two plies, having a thickness being essentially double the thickness of the flange. In the illustrative example, only one side wall of the tube is made with two plies. However, it is also feasible to extend the overlap, thereby forming two, three or four sides with two plies, or to have only part of a side having double plies.

In the embodiments discussed so far, the tube has a cross-section in the form of a parallelogram, and in particular in the form of a square or rhombus. However, the tubular body, when in an erected use state, may have other polygonal cross-sections. Some exemplary other polygonal cross sections useable in embodiments of the extension tube are illustrated schematically in FIGS. 3-5.

Figure 3:
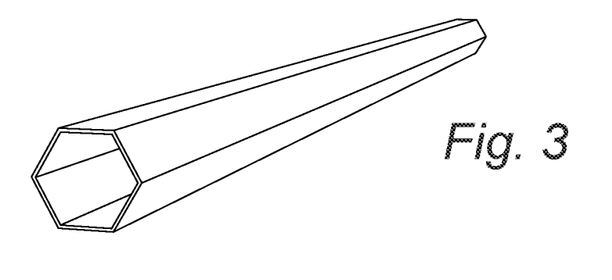
FIGS. 3, 4, 5a and 5b are perspective views illustrating extension tubes in an erected use state in accordance with other embodiments.

In the embodiment of FIG. 3, the cross section of the extension tube is shaped as a hexagon, with six folding lines, defining six sidewall sections. The sidewall sections may have the same length in the cross-section, forming a regular hexagon, but the sides may also be of different lengths. However, preferably any two opposing sides preferably have the same length.

Figure 4:
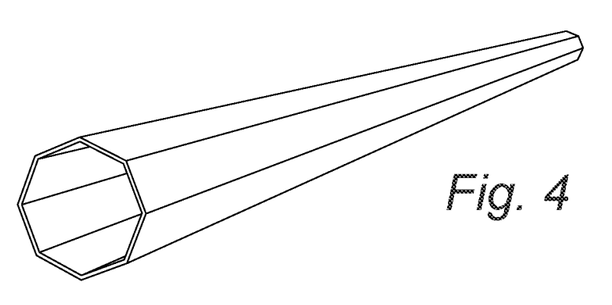

In the embodiment of FIG. 4 the cross section of the extension tube is shaped as an octagon, with eight folding lines, defining eight sidewall sections. The sidewall sections may have the same length in the cross-section, forming a regular octagon, but the sides may also be of different lengths. However, preferably any two opposing sides preferably have the same length.

Figure 5A:
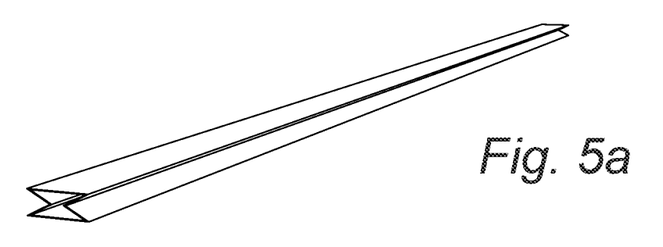

In the embodiment of FIG. 5a, the cross-section of the extension tube is also shaped as a hexagon, but with an hourglass shape, forming a concave irregular hexagon. Again, the sidewall sections may have the same length in the cross-section, but the sides may also be of different lengths. However, preferably any two opposing sides preferably have the same length. In this embodiment, the folding of the concave part of the hexagon occurs inwardly, making the compacted storage state more compact in width but less compact in height.

In all the embodiments discussed so far, the extension tube has a plurality of fold lines, forming a cross-sectional shape in the form of a polygon. However, embodiments with fewer fold lines may also be used. For example, the tube may comprise only two fold lines, which may be compressed towards each other in the erected use state, thereby forming sides extending as arches between the two fold lines. In yet another alternative, there is no fold lines at all.

Figure 5B:
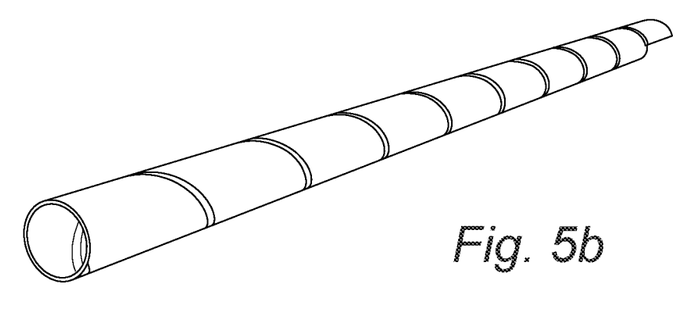

Such an embodiment, without any fold lines, is illustrated in FIG. 5b. Here, the tube has a generally circular cross-sectional shape, but other shapes, such as oval or elliptic, may also be provided. The tube is preferably provided with some memory in the material, so that it resumes an erected state when not forced into a compacted storage state.

Such a tube with circular cross section may be formed in the same way as the previously discussed embodiments, by adhering two free ends of a sheet together. However, for increased stability and robustness, the tube may also be formed by adhering a strip of material together in a helical manner, as in the illustrative example.

Figure 6A:
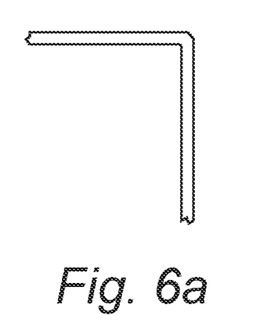
FIGS. 6a-c are side-views illustrating fold lines without any crease (FIG. 6a), with an inwardly protruding crease (FIG. 6b) and an outwardly protruding crease (FIG. 6c), in accordance with embodiments of the present invention; \
Figure 6B:
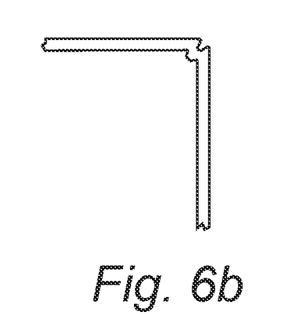
Figure 6C:
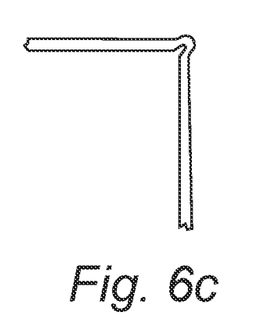

The folding lines may be provided in the form of creased folding lines, as illustrated in relation to FIGS. 6a-c. The creased folding lines are provided with an indentation or protrusion at the center of the folding line, forming a convex or concave bead in the folding line. In FIG. 6a, a fold without any crease is illustrated, whereas FIG. 6b illustrate a fold line with an inward, concave crease, and FIG. 6c illustrate a fold line with an outward, convex crease. Such creasing may be used for all the fold lines, but may alternatively only be used for some of the fold lines, such as for two adjacent fold lines, or for two opposed fold lines.

The extension tube may be formed by a single sheet of material, either comprising a single layer or two or more layers. To form a tube, two sides of the sheet may be connected to each other, preferably with an overlap to provide a strong connection. The connection may be formed by an adhesive, such as a hot melt adhesive. The adhesive is preferably biocompatible.

Figure 7A:
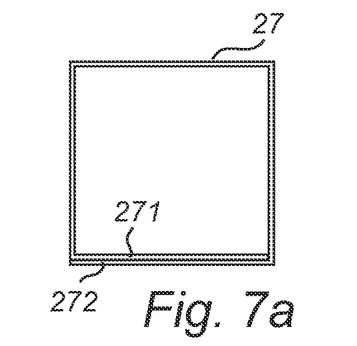
FIGS. 7a-c are cross-sectional views illustrating an extension tube formed by a single sheet of material, and having an overlap in the connection area extending over one side (FIG. 7a), two sides (FIG. 7b), and one side and a half side on each side of this (FIG. 7c), in accordance with embodiments of the invention.
Figure 7B:
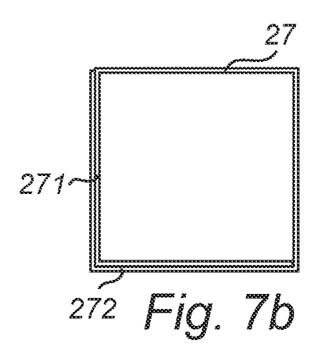
Figure 7C:
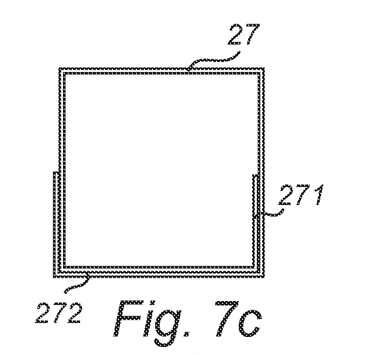

Such embodiments are illustrated schematically in FIGS. 7a-c. In the embodiment of FIG. 7a, a sheet is folded so that the two ends 271 and 272 overlap each other over essentially the length of one side. In the embodiment of FIG. 7b, a greater overlap between the ends 271 and 272 is provided, extending over essentially the length of two sides. In the embodiment of FIG. 7c, the same length of the overlap as in FIG. 7b is provided, but here extending over one full side, and over essentially half a side on each side of this full side.

Figure 8A:
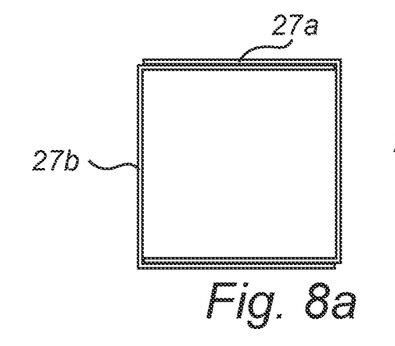
FIGS. 8a-b are cross-sectional view illustrating an extension tube formed by two sheets of material (FIG. 8a) and three sheets of material (FIG. 8b), in accordance with embodiments of the invention.
Figure 8B:
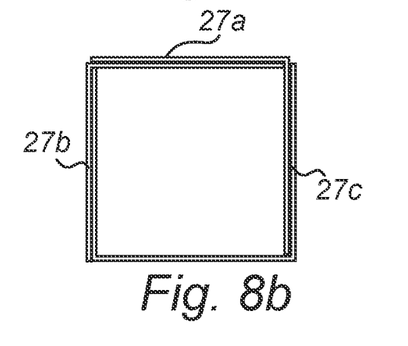

Further, it is also possible to form the extension tube by two or more sheets, instead of only one. Such embodiments are illustrated in FIGS. 8a and 8b. In the embodiment of FIG. 8a, the tube is formed by two sheets 27a and 27b, which are both folded into U-shaped cross sections, each including two fold lines, and arranged inserted into each other, so that a connection, and double plies, are provided on every other side of the tube. In the embodiment of FIG. 8b, the tube is instead formed by three sheets 27a, 27b and 27c. Here, two of the sheets, 27a and 27b, are formed with single fold lines, forming L-shaped cross sections, and the third sheet is provided with two fold lines, and a generally U-shaped cross section. However, other alternatives, such as four sheets, each having L-shaped cross sections, are also feasible.

Figure 9A:
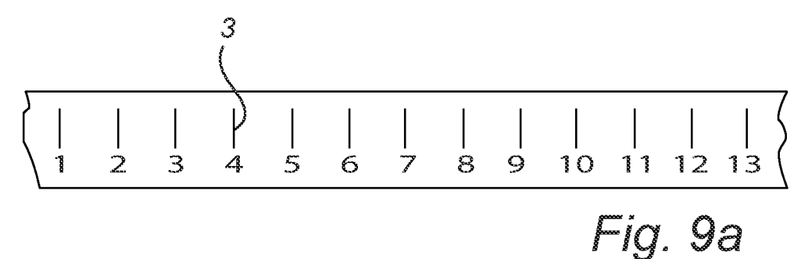
FIGS. 9a-c are top-view of extension tubes having length markings, in accordance with different embodiments of the present invention.

The extension tube may also be provided with markings indicating a length along the longitudinal, axial direction of the extension tube. Such markings may e.g. be in the form of a scale, with numbers indicating various lengths in e.g. cm or inches, similar to the scale on a ruler, as illustrated schematically in FIG. 9a. In this embodiment, a numbered marking 3 is provided for every cm.

Figure 9B:
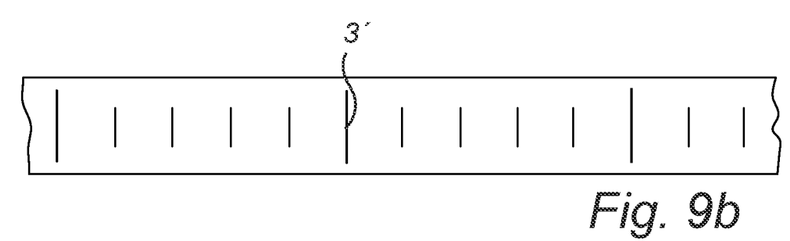

In alternative embodiments, the marking is only graphical, without any numbers, such as illustrated in FIG. 9b, where the marking 3' comprises one type of graphical symbol, here a longer line, arranged with a first, longer distance between each other, such as being separated by 5 cm, and another graphical symbol, such as shorter lines, arranged with a second, smaller distance between each other, such as being separated by 1 cm.

Figure 9C:
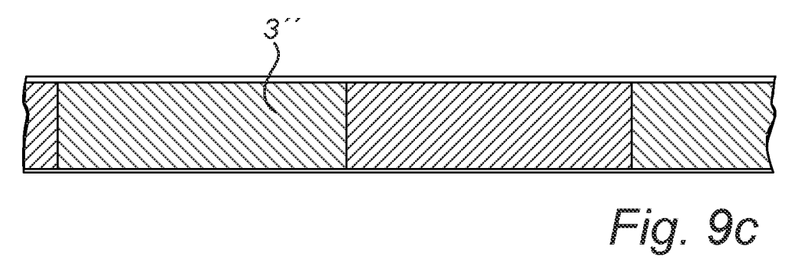

In yet another embodiment, as illustrated in FIG. 9c, the marking 3" is provided in the form of differently colored or differently marked areas, arranged sequentially after each other, and each extending over a certain length, such as over 5 or 10 cm. Two different types of markings A and B may be used, forming a sequential order of A-B-A-B- . . . . However, three or more different types of markings may also be used, forming e.g. the sequential order of A-B-C-D-A-B-C-D-A- . . . .

The marking areas may e.g. be in the form of different colors, such as red and blue, or light grey and dark grey, but may also be in the form of different hatching and the like.

To maintain an inserted discharge end of a catheter in place in the inlet opening during use, the friction between the extension tube and the discharge end may often be sufficient, and additionally or alternatively, the user may manually hold the extension tube in place over the discharge end of the catheter by pressing it over the discharge end.

Figure 12A:
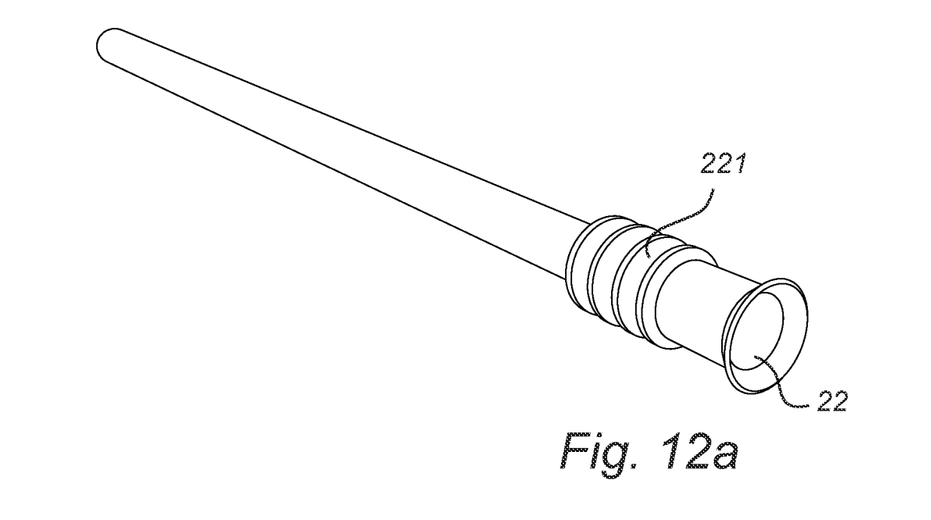
FIGS. 12a-c are cross-sectional views illustrating connection elements at or in the vicinity of the inlet opening of the extension tube, in accordance with embodiments of the present invention.
Figure 12B:
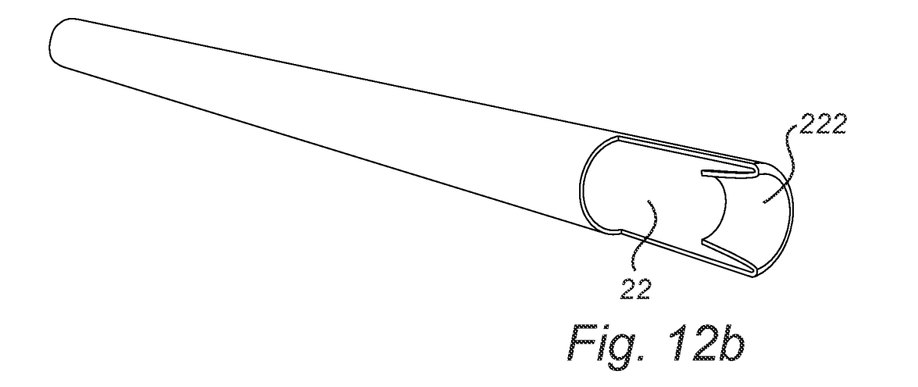

However, the connection may also be enhanced by addition of additional connecting elements. For example, the extension tube may be provided with corrugations 221 in the vicinity of the inlet opening 22, to increase the friction to the discharge end, as illustrated in FIG. 12a. Additionally or alternatively, a flange 222, e.g. provided as in inward folding of the extension tube, may be provided at or in the vicinity of the inlet opening, as illustrated in FIG. 12b. In the exemplary embodiments of FIGS. 12a and 12b, the illustrated extension tube has a circular cross-section. However, the same and similar types of additional connecting elements can also be used for any other cross-sectional type, such as any of the polygonal cross-sections discussed in the foregoing.

Figure 12C:
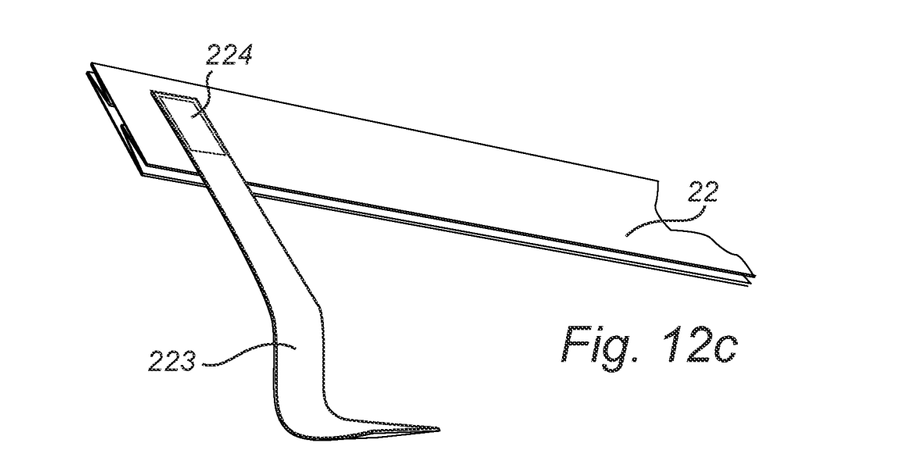

Additionally, or alternatively, the additional connecting elements may be in the form of e.g. a rubber band arranged over the extension tube, compressing the extension tube over the discharge end of the catheter, or as a strap 223, as illustrated in FIG. 12c, which may be wrapped around the extension tube when in place over the discharge end of the catheter, and connectable to itself by e.g. an adhesive area 224.

Many other connection elements are feasible, as would be readily appreciable by someone known in the art.

Use of the Extension Tube

When the extension tube is to be used, the extension tube is removed from any package in which it may be arranged, or dispelled from a dispenser (as will be discussed in more detail in the following). The extension tube may also be severed into a suitable, desired length.

Figure 10:
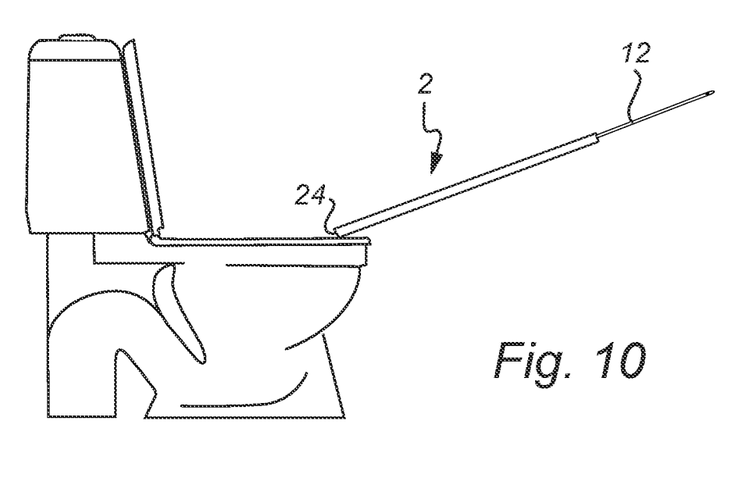

The extension tube is then erected into the erected use state, and can thereby function as an extension tube. The discharge end 12 of the urinary catheter, of which the insertable section 11 may have been already inserted into the urethra of the user, is then placed in the inlet opening 22 of the extension tube. The outlet opening 23 is arranged at the rim of the toilet, or any other appropriate position, so that urine could be drained into the desired location. This is illustrated schematically in FIG. 10. Hereby, a prolongation of the fluid path of the urinary catheter is provided, and the drained urine can be discharged into e.g. a toilet even when the user is at some distance from the toilet.

The extension tube may be arranged to remain in place over the end of the catheter by means of friction between the internal sides of the extension tube and the external walls of the catheter discharge end. To increase this friction, the extension tube may also be provided with friction enhancing elements, such as an internal coating with increased friction close to the inlet end, corrugations, a flange, or other type of indenting or protruding parts to interact with the catheter discharge end, or the like.

Additionally, or alternatively, the user may manually hold the extension tube in place over the catheter discharge end during use, e.g. by pressing the extension tube towards the catheter discharge end with a two finger grip or the like.

Additionally, or alternatively, an external connection element may also be used, such as a rubber band, an adhesive tape, a strap, or the like, in case a tighter seal is desired.

After use, the extension tube may be directly discarded. However, it may prior to that be at least to some extent compacted again, thereby making it less noticeable if discarded. Alternatively, the again compacted extension tube may also be arranged in a storage package, and then be carried by the user in the same discrete way as before use, to be discarded later.

Since the material of the extension tube is to a large, or very large, extent made of cellulose, it can, depending on the composition, be made to disintegrate after a relatively short time when immersed in water. This makes it possible also to discard the extension tube also in the toilet, to flush it down. In doing so, the extension tube will after a while disintegrate similar to ordinary toilet paper.

Material of the Extension Tube

Figure 11A:
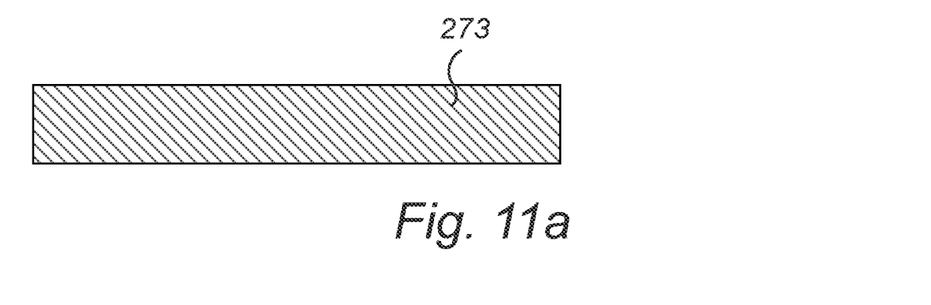
FIGS. 11a-d are cross-sectional view illustrating various embodiments of materials forming the extension tube having one or more layers, in accordance with embodiments of the invention.

The extension tube may be formed of one or several sheets made of a single cellulose-based layer, referred to as the first layer 273, as illustrated schematically in FIG. 11a.

Figure 11B:
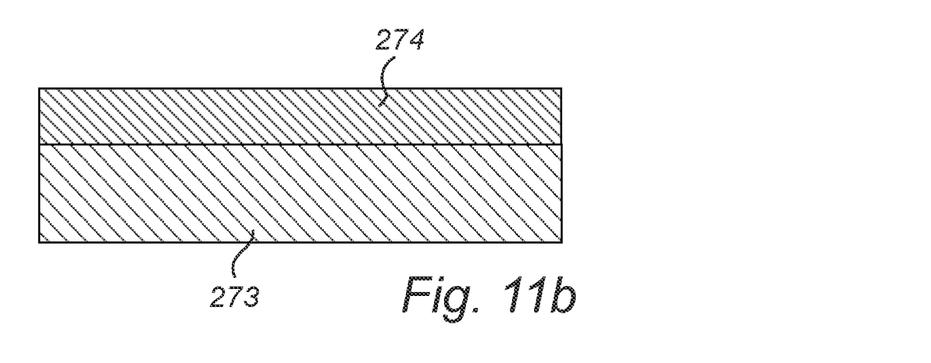

However, in other embodiments, the sheet material may comprise one or more additional layers, such as in the form of a laminated second cellulose-based material 274, as illustrated in FIG. 11b.

Figure 11C:
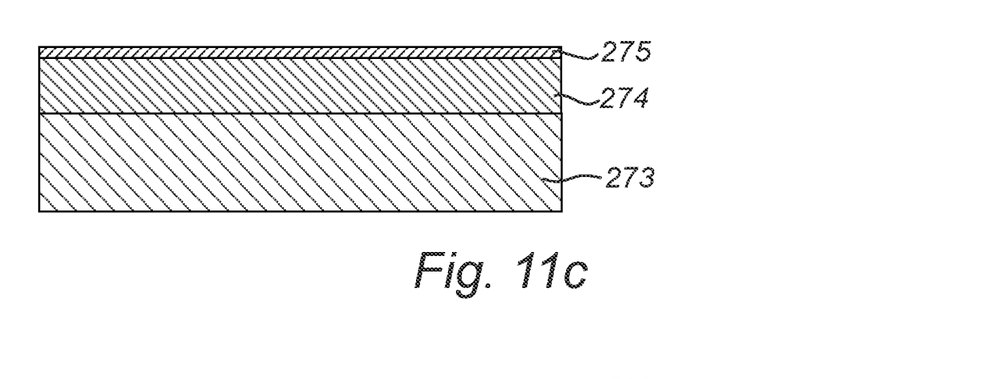
Figure 11D:
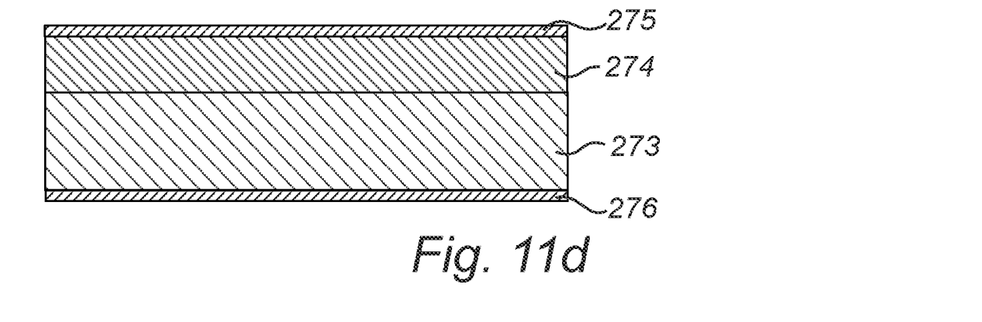

Additionally, or alternatively, the sheet material may also comprise a non-cellulose-based layer, such as a thin polymeric film or coating. FIG. 11c illustrate an embodiment where such a thin film or coating 275 is arranged on top of the second cellulose-based material 274. FIG. 11d illustrate an embodiment where a thin coating or film 276 is also arranged on the opposite surface, on the lower side of the first cellulose-based material 273.

However, other combinations are also feasible, such as only a thin polymer film or coating arranged on the first cellulose-based layer, etc.

The first layer may include at least 40 wt % of natural and/or regenerated cellulose fibers, and preferably at least 50 wt % of natural and/or regenerated cellulose fibers, such as at least 60 wt %, at least 70 wt %, at least 80 wt %, at least 90 wt %, or at least 95 wt %.

In one embodiment, the first layer is made primarily of natural cellulose fibers. In a preferred embodiment, the first layer is made of paper.

The material of the extension tube is preferably chosen and arranged so that the extension tube remains relatively intact and stable when water or urine flows through its internal lumen during a determined use time period, i.e. at least for a period of time sufficient to drain urine from the bladder, such as for at least 5 minutes, and preferably at least 10 or 15 minutes. Preferably, the material is also arranged to resist, at least to a large extent, transfer of moisture from the interior surface of the extension tube to the exterior surface during this determined use time period.

At the same time, the material of the extension tube is preferably hydrodegradable, and chosen and arranged so that the extension tube to a large extent disintegrates when immersed in water, such as within a period of time sufficient to make the extension tube flushable. For example, the extension tube could be arranged to be sufficiently disintegrated when immersed in water for a few hours or less.

An additional layer may also be a cellulose-based layer, but preferably having at least to some extent different properties than the first cellulose-based layer, such as being more water resistant and/or having more rigidity. Any such additional cellulose-based layer preferably may also include at least 40 wt % of natural and/or regenerated cellulose fibers, and preferably at least 50 wt % of natural and/or regenerated cellulose fibers, such as at least 60 wt %, at least 70 wt %, at least 80 wt %, at least 90 wt %, or at least 95 wt %.

In one embodiment, all layers of the sheet or sheets forming the extension tube are cellulose-based layers.

However, an additional layer may also be made of a non-cellulose based material, such as a thin coating of thermoplastic polymer.

In addition to the cellulose fibers, the cellulose based material, and in particular the first material, may comprise additives, such as one or more of fillers, pigments, wet strength chemicals, retention chemicals, cross-linkers, softeners or plasticizers, adhesion primers, wetting agents, biocides, optical dyes, hydrophobizing chemicals such as alkyl ketene dimer (AKD), alkyl succinic anhydride (ASA), waxes, resins etc.

Preferably, all the cellulose based layers contain primarily cellulose and optional fillers. The content of any additional additives is preferably less than 20 wt %, and more preferably less than 15 wt %, and more preferably less than 10 wt %, and most preferably less than 5 wt %.

The fillers may be any fillers known to be used in papermaking, such as mineral fillers like kaolin, china clay, titanium dioxide, gypsum, talc, chalk, ground marble, ground calcium carbonate and precipitated calcium carbonate.

One or more sizing additives, such as e.g. rosin, liquid paraffin wax, alkyl ketene dimer (AKD), alkyl succinic anhydride (ASA), etc., may be added to the cellulose material to provide a desired absorbency profile for the material.

In embodiments where AKD is used, the content of AKD is preferably in the range of 0.1-10 wt %, and preferably in the range 0-5-5%, and most preferably in the range 1-2 wt %.

In embodiments where poly(lactic acid) (PLA) is used, the content of PLA is preferably in the range of 0-50 wt %, and preferably in the range of 1-45 wt %, and more preferably in the range of 5-40 wt %, and even more preferably in the range of 10-35 wt %, and most preferably in the range of 20-30 wt %. Inclusion of PLA in the material makes the material more rigid.

The wet strength additives may e.g. be polymers, such as polyacrylic amide (PAM), or starch.

In a preferred embodiment, there is a high content of cellulose, and only additives to increase the hydrophobicity and optional fillers are added.

The cellulose based material can be produced in a papermaking machine, such as any conventional type of machine known to the skilled person used for the production of paper, paperboard, or similar products. The material is formed as a wet web, which is then dried. In order to increase the shape stability and memory of the material, the dewatering may occur in an at least partly shaped and erect form, such as by being placed on suitably arranged wires. The dewatering may also include subjecting the web to heat, vacuum, ultrasound or the like. After dewatering and drying, the material may also be dried or smoothened by soft or hard nip, calendrers etc.

The cellulose fibers of the material may be wood cellulose fibers, both from hardwood and/or softwood fibers. However, the cellulose may also be from other sources, such as agricultural fibers such as wheat straw pulp, bamboo, bagasse, or other non-wood fiber sources. The material is preferably made from pulp including pulp from virgin fiber, e.g. mechanical, chemical and/or thermomechanical pulps. It can also be made from broke or recycled paper, i.e. recycled cellulose fibers.

The material may also include nanocellulose, such as a cellulose nanofiber material containing multiple elementary fibrils with both crystalline and amorphous regions. In this case, the nanocellulose may be included together with other cellulose in a layer, or arranged in a separate layer. By using nanocellulose the material becomes more stable and rigid in shape, with an increased shape memory, and is also more water resistant than other cellulose materials. The nanocellulose may be wood- or plant-based, and may be chosen from cellulose nanofibrils (CNF) or cellulose nanocrystals (CNC), preferably cellulose nanofibrils. This ensures that the raw materials for the cellulose product are obtained from an abundant, renewable and biodegradable source.

The sheet material forming the extension tube, regardless of whether it is a single layer material or a laminated material having two or more layers, preferably has a surface weight in the range of 90-130 g/m$^2$. If the cellulose has thicker and longer fibers, a thinner material, may be provided, having essentially the same properties.

In embodiments where a single cellulose based layer is used, i.e. only the first layer, it preferably has an absorbance, measured as a Cobb-60 value, in the range of 5-50 g/m$^2$. Preferably, the Cobb-60 value is in the range of 10-30 g/m$^2$, and most preferably in the range 10-20 g/m$^2$.

In embodiments where two or more cellulose based layers are used, the inner layer may have a lower Cobb value, and the outer layer may have a higher Cobb value. In such embodiments, the inner layer may have a Cobb-60 value in the range of 5-50 g/m$^2$, and preferably in the range 10-30 g/m$^2$, and most preferably in the range of 10-20 g/m$^2$. The outer layer may have a Cobb-60 value in the range of 50-150 g/m$^2$, and preferably in the range 70-130 g/m$^2$, and most preferably in the range of 80-110 g/m$^2$.

In one embodiment, the Cobb-60 value on the inside surface is preferably less than 30 g/m², and the Cobb-60 value on the outside surface is preferably more than 100 g/m².

The material of the tubular body is preferably arranged to be more water resistant, and have greater water repellency, on the internal surface, i.e. facing the internal lumen, than in the middle of the wall, and/or on the external surface.

To this end, a chemical surface sizing agent, surface treatment agent or the like may be added to the internal surface, and optionally also to the external surface. For example, the surface can be made more hydrophobic using a biobased composition.

Additionally, or alternatively, when a laminated material is used, the inner layer may be a cellulose based layer having less absorbency, and greater water resistance, than another layer, such as an outer layer and/or an intermediate layer.

In another embodiment, when a laminated material is used, a thin layer of a hydrophobic organic material or the like, such as poly(lactic acid) (PLA), may be arranged on the interior surface, as a coating. It is also possible to use a silicone-based layer, starch-based layer, clay-based layer, polyethylene (PE) layer, or other thermoplastic polymer layers, and the like. Instead of being laminated, such a layer may also be provided in the form of spray or dip coating, or the like. A layer including nano-cellulose may also be used towards the interior surface.

The sheet material forming the extension tube is preferably biodegradable and non-toxic.

Extension Tube Assembly with a Dispenser

The extension tubes may be packed individually in separate packages, for example as rolls, as discussed in the foregoing.

Alternatively, a plurality of extension tubes may be packed together in a package, such as 5 or 10 extension tubes in one package. In this case, the package may be re-closable, so that the package may be closed after each removal of an extension tube from the package.

The extension tubes may be provided in a length sufficient for most users, such as having a length in the range of 30-70 cm, and preferably in the range of 35-65 cm, and more preferably in the range of 40-60 cm. If a shorter extension tube is required, the user may cut or otherwise sever a part of the extension tube, e.g. with the use of the above-discussed markings.

However, the extension tube may also be provided in much longer lengths, allowing the user to cut the extension tube into any desired length for every use occasion. In such an embodiment, a roll of extension tube may comprise a very long extension tube, e.g. in a length of several meters or more, allowing the user to cut off or sever an extension tube of a suitable length for every occasion, again e.g. with the aid of the above-discussed markings.

For easy handling of such a long extension tube, a dispenser may be provided, arranged to house the extension tube arranged in a compacted state in a roll. The roll is preferably rotatably arranged within the housing, and the dispenser preferably comprises a cutter for severing a length of dispensed extension tube from said roll.

With the dispenser, the user may at every time dispense and sever the desired length of the extension tube. This is even more facilitated when markings are provided on the extension tube.

The roll may comprise an extension tube sufficient for multiple uses. For example, the roll may comprise an extension tube of a length of a meter or more, such as 2 m or more, 5 m or more, or even longer.

The dispenser is preferably arranged to enable replacement of the roll of the extension tube. Hereby, the dispenser may be reused over time.

The cutter may be arranged as a fixed serration, as in a conventional adhesive tape dispenser, whereby the extension tube may be pulled downwards towards the serration to make the cut.

In an alternative embodiment, the cutter may comprise a hinged, jaw-like serration element, whereby the cutting is made by clamping the cutter over the extension tube to sever it.

Figure 13A:
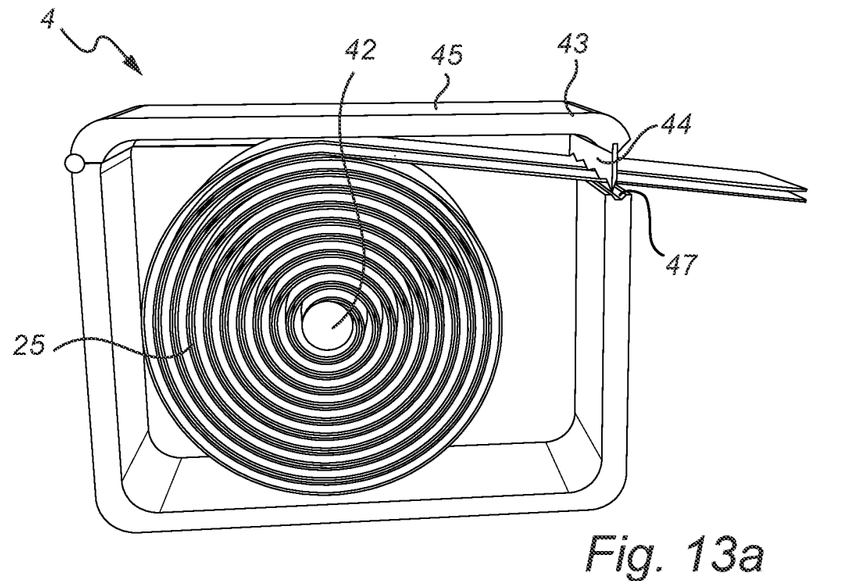
FIG. 13a is a cross-sectional view of the dispenser.
Figure 13B:
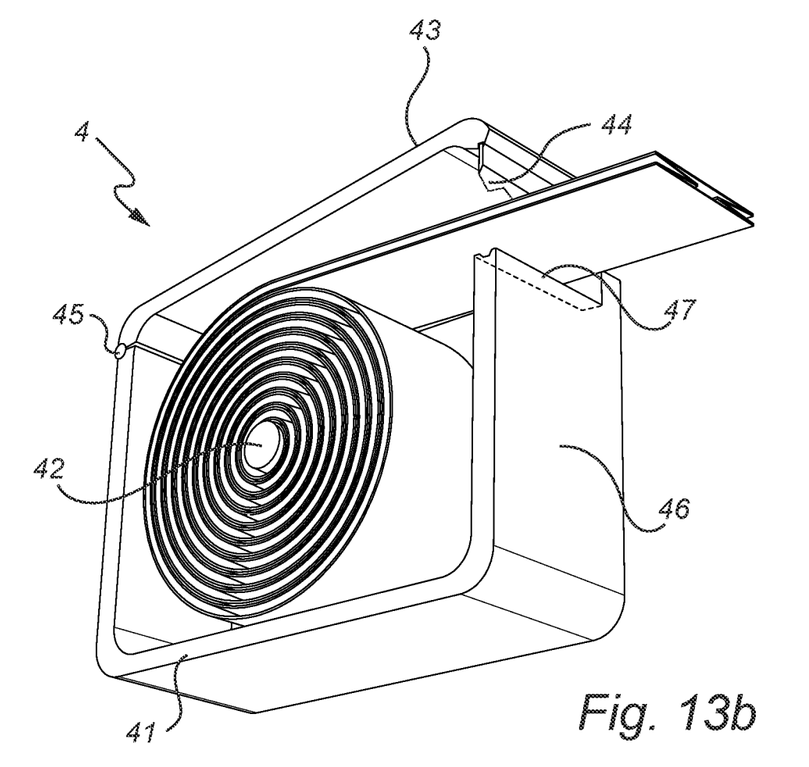
FIG. 13b is a perspective view of the dispenser.

In such an embodiment, as illustrated in FIGS. 13a and 13b, the dispenser 4 comprises a housing 41, including an open side and one closed side, as in the illustrative embodiment, or two opposite sides, and with a hub 42 extending from at least one side. The hub 42 is adapted to hold a roll 25 of extension tube for rotation within the housing 41. A bridge, forming a circumferential wall, connects the sides, thereby forming a relatively flat housing, having essentially the thickness of the roll. The bridge may be formed as flanges on the opposite sides, thereby forming the bridge when mating.

The dispenser further comprises a cutter 43 pivotably connected to the bridge, via a hinge 45, and arranged to cut the extension tube. The cutter may comprise a plurality of cutting teeth 44. The teeth are preferably formed integrally with the cutter, and of the same material, such as a plastic material. However, the teeth may also be formed as a separate component, and may be of a different material, such as a metal. The teeth are preferably triangular in shape, and 3-10 teeth may be provided, such as 3-6 teeth. However, instead of teeth, the cutter may also have other types of blades to affect the cutting.

The housing preferably forms a channel 47 for receiving the teeth 44 of the cutter for releasably retaining the extension tube in position to cut it with the cutter. The channel 47 preferably extends substantially across the width of the housing, in a direction generally parallel with the hinge 45 connecting the cutter 43 to the bridge. The channel is preferably sufficiently deep to completely receive the teeth 44. The channel is preferably sufficiently wide to receive the teeth as they traverse an arc when the cutter 43 is moved to its closed position.

The cutter may be maintained in a closed position by a snap-lock arrangement or the like.

The hub 42 may comprise a single hub, or two hub portions, one extending from each side of the housing, the hub portions interlocking to form the hub.

The dispenser is preferably minimally larger than the roll of extension tube held by the dispenser. In an embodiment, the dispenser is of a palm size, thereby making it easy to use and easy to carry around. Preferably, the dispenser is minimally larger than the roll of extension tube held by the dispenser. The dispenser is further preferably arranged to be operable by only one hand, e.g. using the thumb for operating the cutter.

The pivotable cutter 43 may also function as a lid and closure of the housing, to substantially completely enclose the roll within the housing.

The dispenser is cost-efficient to produce and convenient to use. The housing may e.g. be produced by a single piece of material.

The dispenser could be used either as a disposable unit used with only one roll of extension tube, or as a reusable unit that is reloaded with new rolls 25 of extension tube after the previous roll is used.

In a preferred embodiment, the housing is preferably open or openable, to allow exchange of the roll, so that the dispenser is re-useable. For example, the housing may comprise an open side, as in the illustrative example. Alternatively, it may comprise a removable side wall, functioning as a lid, and which is removable for replacing the roll. In yet another alternative, the housing may comprise a hinge formed in the bridge between the two opposing side-walls, and preferably at a position opposite to the cutter, allowing the opposing side walls to be folded away from each other for opening of the housing. Thus, the two opposing side walls may be fixedly connected to each other over the bridge only over the hinge, and apart from that being closed by a non-fixed separable closure. Locking tabs or the like may be provided to maintain the housing closed, and may e.g. function as a snap-lock. However, other locking arrangements may also be used.

The dispenser is preferably constructed from inexpensive plastic material, such as polystyrene, polypropylene, polyethylene, polycarbonate, or the like.

Concluding Remarks

Specific embodiments of the invention have now been described. However, several alternatives are possible, as would be apparent for someone skilled in the art. For example, different types of cellulose based material may be used, and may also be combined with layers which are non-cellulose based. Further, the extension tube may be configured in various ways, e.g. having different types of polygonal cross-sections. Further, the extension tubes may be provided in single lengths, or arranged together in a long extension tube, from which an adequate length is severed of before use, e.g. with the aid of a dispenser. Further, the dispenser may be configured in various ways.

Such and other obvious modifications must be considered to be within the scope of the present invention, as it is defined by the appended claims. It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting to the claim. The word "comprising" does not exclude the presence of other elements or steps than those listed in the claim. The word "a" or "an" preceding an element does not exclude the presence of a plurality of such elements. Further, a single unit may perform the functions of several means recited in the claims.

The invention claimed is:

1. An extension tube for a urinary catheter, comprising a tubular body with an inlet opening, an outlet opening and an internal lumen extending between said inlet opening and said outlet opening, wherein the tubular body has a length in the range of 30-70 cm and, in an erected state, a maximum cross-sectional extension in the range of 0.5-3 cm, said tubular body comprising at least a first layer, said first layer including natural and/or regenerated cellulose fibers, and wherein the tubular body is arranged to be compressible into a generally flat compacted storage state, and to be expandable into an expanded, tubular use state, wherein the tubular body has a plurality of longitudinally extending fold lines, extending along an axial direction of the tubular body, wherein the tubular body is arranged to remain intact and stable during a flow of water or urine through the internal lumen for at least 5 minutes.

2. The extension tube of claim 1, wherein said first layer includes at least 40 wt % of natural and/or regenerated cellulose fibers.

3. The extension tube of claim 1, wherein said first layer includes at least 70 wt % of natural and/or regenerated cellulose fibers.

4. The extension tube of claim 1, wherein said first layer includes at least 90 wt % of natural and/or regenerated cellulose fibers.

5. The extension tube of claim 1, wherein said first layer is made primarily of natural cellulose fibers.

6. The extension tube of claim 5, wherein the first layer is made of paper.

7. The extension tube of claim 1, wherein said first layer comprises regenerated cellulose fibers.

8. The extension tube of claim 7, wherein the regenerated cellulose fibers are viscose.

9. The extension tube of claim 1, wherein the tubular body is formed by the first layer as a single layer.

10. The extension tube of claim 1, wherein the tubular body comprises at least one additional layer, said additional layer forming a laminated construction with said first layer.

11. The extension tube of claim 1, wherein at least two of the plurality of longitudinally extending fold lines are arranged oppositely to each other, separated by the same circumferential distance along the tubular body in both directions.

12. The extension tube of claim 1, wherein at least one of the plurality of fold lines is provided with a crease, to form a creased fold line.

13. The extension tube of claim 1, wherein the tubular body, in the erected use state, has a polygonal cross-section.

14. The extension tube of claim 1, wherein the tubular body, when in the erected use state, has a quadrilateral cross-section.

15. The extension tube of claim 14, wherein the tubular body, when in the erected use state, has a cross-section formed as a parallelogram.

16. The extension tube of claim 1, wherein the tubular body has a length in the range of 40-60 cm.

17. The extension tube of claim 1, wherein the extension tube is provided with markings indicating a length along the axial direction of the extension tube.

18. The extension tube of claim 1, wherein the tubular body, in an erected state, has a maximum cross-sectional extension in the range of 1-2.5 cm.

19. An extension tube assembly, comprising:
an extension tube in accordance with claim 1, wherein the extension tube is arranged in a compacted state in a roll; and
an extension tube dispenser for housing said roll, and comprising a cutter for severing a length of dispensed extension tube from said roll.

20. The extension tube of claim 1, wherein the material forming the extension tube has a surface weight in the range of 50-180 g/m$^2$.

21. The extension tube of claim 1, wherein the tubular body further comprises a flange extending along the full length of the tubular body and protruding away from the internal lumen.

22. The extension tube of claim 1, further comprising friction enhancing elements arranged on an internal side of the extension tube to increase the friction between the extension tube and a therein introduced catheter.

* * * * *